United States Patent
LaTorraca et al.

(10) Patent No.: US 11,348,673 B2
(45) Date of Patent: May 31, 2022

(54) SYSTEM AND METHOD FOR DISTRIBUTED MEDICATION MANAGEMENT

(71) Applicant: CAREFUSION 303, INC., San Diego, CA (US)

(72) Inventors: Gary John LaTorraca, San Diego, CA (US); Brendan John Burgess, Poway, CA (US)

(73) Assignee: CAREFUSION 303, INC., San Diego, CA (US)

(*) Notice: Subject to any disclaimer, the term of this patent is extended or adjusted under 35 U.S.C. 154(b) by 203 days.

(21) Appl. No.: 16/004,311

(22) Filed: Jun. 8, 2018

(65) Prior Publication Data

US 2019/0378602 A1    Dec. 12, 2019

(51) Int. Cl.
*G16H 20/13* (2018.01)
*G06Q 10/08* (2012.01)
(Continued)

(52) U.S. Cl.
CPC ............... *G16H 20/13* (2018.01); *A61J 1/03* (2013.01); *A61J 7/0084* (2013.01);
(Continued)

(58) Field of Classification Search
CPC .................. G06F 1/00–2221/2153; G06Q 10/00–2250/905; H02J 1/00–2310/70
See application file for complete search history.

(56) References Cited

U.S. PATENT DOCUMENTS 7,630,789 B2 * 12/2009 Broadfield ........... A61G 12/001 221/98
9,492,355 B2 * 11/2016 Ratnakar ................ G07F 9/02
(Continued)

FOREIGN PATENT DOCUMENTS

AU      2013209818 B2 *  7/2013
CA         2954045 A1 *  1/2016 ........... G06Q 10/087
(Continued)

OTHER PUBLICATIONS

Hsu et al., "Application of RFID Technology in Management of Controlled Drugs—Proof of Concept," Proceedings of WMMP 2010. © Department of Computer Science, University of Münster 2010 (Year: 2010).*

(Continued)

*Primary Examiner* — Elaine Gort
*Assistant Examiner* — Jonathon A. Szumny
(74) *Attorney, Agent, or Firm* — Morgan, Lewis & Bockius LLP

(57) ABSTRACT

A method including authorizing a user to access a dispensing unit upon receipt of a medication request, is provided. The dispensing unit comprises a storage location with one or more door enclosure storing at least one container. The method also includes providing a visual indicator to the user for a selected container in the storage location with one or more door enclosure, the selected container comprising a medication associated with the medication request, and unlocking the selected container for the user by wirelessly actuating a latch for a lid in the selected container from a mat that is communicatively coupled with the dispensing unit. The method also includes locking the selected container when the user verifies a transaction comprising the medication request, and updating a record and a medication inventory in a remote server based on the transaction. A storage location with one or more door enclosure and a container used in the above method are also provided.

14 Claims, 12 Drawing Sheets

(51) Int. Cl.
*A61J 1/03* (2006.01)
*A61J 7/00* (2006.01)
*H02J 50/90* (2016.01)
H02J 7/02 (2016.01)

(52) U.S. Cl.
CPC ............ *G06Q 10/087* (2013.01); *H02J 7/025* (2013.01); *H02J 50/90* (2016.02)

(56) References Cited

U.S. PATENT DOCUMENTS

| | | | | |
|---|---|---|---|---|
| 9,968,521 | B1* | 5/2018 | Price | G07F 17/0092 |
| 2005/0061877 | A1* | 3/2005 | Stevens | G07C 9/28 |
| | | | | 235/385 |
| 2006/0054682 | A1* | 3/2006 | de la Huerga | G16H 70/40 |
| | | | | 235/375 |
| 2006/0062734 | A1* | 3/2006 | Melker | G16H 80/00 |
| | | | | 424/10.1 |
| 2006/0174129 | A1* | 8/2006 | Brignone | H04L 9/3236 |
| | | | | 713/181 |
| 2007/0290587 | A1* | 12/2007 | Jeansonne | A61G 12/001 |
| | | | | 312/311 |
| 2008/0162192 | A1* | 7/2008 | Vonk | A61J 7/0481 |
| | | | | 705/3 |
| 2008/0319790 | A1* | 12/2008 | Vahlberg | G06F 19/3462 |
| | | | | 705/2 |
| 2010/0200593 | A1* | 8/2010 | Lazar | A61J 7/0481 |
| | | | | 220/560.03 |
| 2010/0305749 | A1* | 12/2010 | Coe | G07F 11/62 |
| | | | | 700/231 |
| 2012/0006708 | A1* | 1/2012 | Mazur | A61J 7/0481 |
| | | | | 206/438 |
| 2012/0158606 | A1* | 6/2012 | Moudy | G06Q 10/0832 |
| | | | | 705/332 |
| 2013/0110283 | A1* | 5/2013 | Baarman | A61J 7/04 |
| | | | | 700/236 |
| 2013/0253291 | A1* | 9/2013 | Dixon | A61G 7/018 |
| | | | | 600/323 |
| 2014/0097197 | A1* | 4/2014 | Nguyen | A61J 1/03 |
| | | | | 221/154 |
| 2015/0005934 | A1* | 1/2015 | Bell | G07F 11/62 |
| | | | | 700/237 |
| 2015/0223890 | A1 | 8/2015 | Miller et al. | |
| 2015/0227127 | A1* | 8/2015 | Miller | G05B 19/042 |
| | | | | 700/244 |
| 2016/0045398 | A1* | 2/2016 | Lai | G07F 9/002 |
| | | | | 206/216 |
| 2016/0104277 | A1* | 4/2016 | Takamori | G01J 3/46 |
| | | | | 382/128 |
| 2016/0158109 | A1* | 6/2016 | Nova | G06F 19/3462 |
| | | | | 206/534 |
| 2016/0314276 | A1* | 10/2016 | Wilz, Sr. | G06F 19/3462 |
| 2017/0095405 | A1* | 4/2017 | Afsarifard | G06F 19/3462 |
| 2017/0228951 | A1* | 8/2017 | Foot | H04W 4/35 |
| 2018/0032699 | A1* | 2/2018 | Carrender | G16H 40/20 |
| 2018/0075216 | A1* | 3/2018 | Nurse | G16H 10/60 |
| 2019/0178815 | A1* | 6/2019 | Tojo | G01N 21/9508 |
| 2019/0223643 | A1* | 7/2019 | Hara | A47G 29/20 |
| 2019/0341136 | A1* | 11/2019 | Hopper | G16H 20/17 |
| 2020/0165024 | A1* | 5/2020 | Vanbiljon | B65C 9/36 |

FOREIGN PATENT DOCUMENTS

| | | | | |
|---|---|---|---|---|
| JP | 2005-267443 A | * | 9/2005 | |
| WO | WO-9960982 A2 | | 12/1999 | |
| WO | WO-2009081206 A1 | * | 7/2009 | ............ A61B 5/296 |
| WO | WO-2010056712 A1 | * | 5/2010 | ............ A61M 5/002 |
| WO | WO-2010066904 A1 | * | 6/2010 | ............ A61J 7/0084 |
| WO | WO-2012102759 A1 | | 8/2012 | |
| WO | WO-2014210061 A1 | | 12/2014 | |
| WO | WO-2016090315 A1 | | 6/2016 | |
| WO | WO-2017066741 A1 | | 4/2017 | |

OTHER PUBLICATIONS

Invitation to Pay Additional Fees and Partial International Search for Application No. PCT/US2019/033349, dated Sep. 10, 2019, 13 pages.

International Search Report and Written Opinion for Application No. PCT/US2019/033349, dated Nov. 11, 2019, 21 pages.

* cited by examiner

SYSTEM AND METHOD FOR DISTRIBUTED MEDICATION MANAGEMENT

BACKGROUND

The present disclosure is generally related to automated medication management for healthcare applications. More specifically, the present disclosure relates to devices and methods that provide more scalable solutions, lower cost, and a smaller footprint to perform automated medication dispensing over a distributed network of healthcare facilities associated with a centralized pharmacy server or cloud.

Some approaches to automated medication delivery from a centralized pharmacy server involve expensive equipment with a large footprint typically located within a single, centralized healthcare facility or hospital, where a local network may provide a fast and efficient medication control process.

SUMMARY

Smaller and more remote facilities still have not implemented automated medication systems, mostly due to the inability of automated medication system offerings to scale to smaller units of dispensing.

A system for automated medication as disclosed herein provides inventory visibility across a continuum of medication distribution. The system uses devices such as a drawer, a lockable container, and a smart mat (that is optionally a gateway) that interact with each other and exchange information (e.g., inventory information) from a centralized pharmacy to a remotely located clinic. The system is highly scalable, as multiple devices may be seamlessly incorporated to a network by instrument identification protocols and multiple wireless connectivity. The system provides a broad reach to multiple devices across all levels of medication distribution. Described herein are further embodiments that relate to similar principles as described above.

In a first embodiment described herein, a method includes authorizing a user to access a dispensing unit for the purpose of dispensing or loading medications. The dispensing unit includes a storage location with a door enclosure, or other securable storage location. The method further includes storing at least one container and providing a visual indicator to the user for a selected container that includes a medication associated with the medication request in the storage location with the door enclosure, or other securable storage location. The storage location with door enclosure, or other securable storage location, can be securely unlocked using identity management and then activating a latch, which may be done wirelessly. The method further includes unlocking the selected container for the user by wirelessly actuating a latch for a selected container from a smart mat that is coupled with the container, and locking the selected container when the user verifies a transaction including the medication request. The method also includes updating a record and a medication inventory in a remote server based on the transaction. In some embodiments, the transaction record may be synchronized with the server at a later time, when connectivity is not immediately available. In some embodiments, a transaction record is synchronized with the server at a later time if connectivity is not immediately available.

In further embodiments, a device includes a surface configured to receive a mobile smart container or device configured to store medications to be dispensed to a patient. The device includes a charging device configured to wirelessly provide power to the mobile smart container or device, and an antenna configured to receive an identification signal from the mobile smart container or device. The device also includes a processor configured to determine a medication content of the mobile smart container or device, and a communications module configured to update a medication inventory in a centralized pharmacy server based on the medication content of the mobile smart container or device.

Another embodiment includes a storage location with a door enclosure or a location to store at least one container having an identification tag, with an electronically actuated latch. The device also includes an antenna configured to scan for the identification tag in the enclosure is closed, a processor, configured to control the antenna and to process an information received in the antenna, and a communications module to update a database in a remote server based on a content of the at least one container and processed by the processor.

BRIEF DESCRIPTION OF THE DRAWINGS

In the figures, elements having the same or similar reference numeral have the same or similar functionality or configuration, unless expressly stated otherwise.

DETAILED DESCRIPTION

Figure 1:
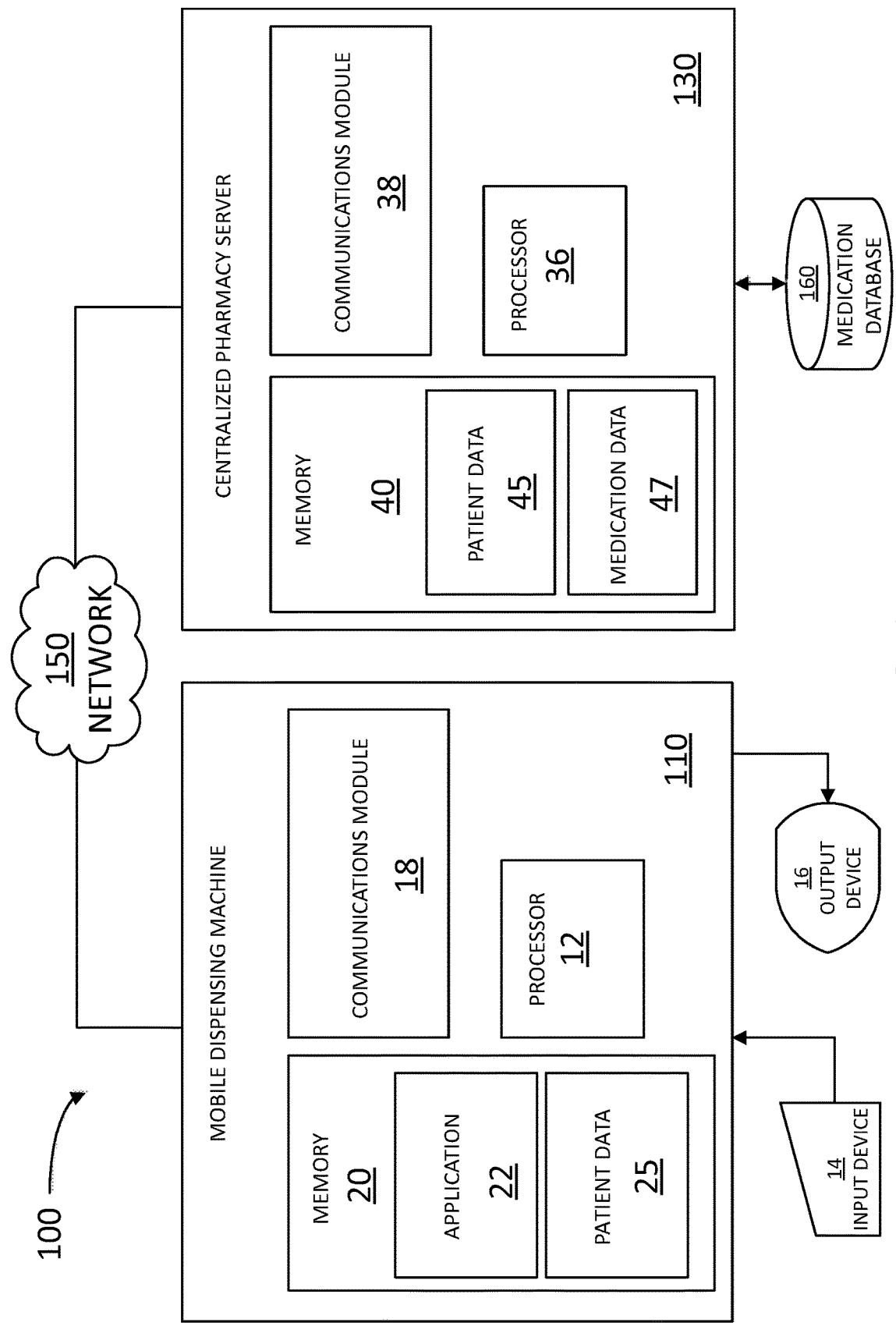
FIG. 1 illustrates a system for distributed medication management, according to some embodiments.

The present disclosure is related to medication delivery systems, associated devices, and methods of use of the above. More specifically, some of the embodiments disclosed herein include methods for dispensing medications and for medication management including large, centralized units located in acute care units (e.g., large hospitals, specialized clinics, and the like) that distribute medications to dispensing systems located in smaller, remotely located facilities (e.g., physician offices in remote villages or towns, nursing homes, and the like).

A system for automated medication as disclosed herein provides inventory visibility across multiple levels of the medication distribution. The system uses devices such as a drawer, a lockable container, and a smart mat that interact with each other and exchange information (e.g., inventory information) and updates across multiple levels of medication distribution from a centralized pharmacy to a remotely located clinic. In some embodiments, a healthcare professional requests access to a storage location with one or more door enclosures in an automated dispensing machine (ADM). The ADM, after validating authorization credentials from the healthcare professional, opens the storage location with one or more door enclosures, which may include multiple smart, lockable containers storing multiple medication orders, each container including a display with a visible indicator. The smart, lockable containers are mobile smart container or devices wirelessly communicable with other devices and with a network. A smart, lockable container may use the visible indicator to signal the healthcare professional that the desired medication is stored within, and automatically unlock, for access. The storage drawer or storage location can be securely unlocked using identity management and then wirelessly activating a latch. After retrieving the medication, the smart, lockable container automatically locks, and transmits updated medication inventory information to a centralized pharmacy server. In this regard, user access to medication content is prevented to unauthorized users. In some configurations, the storage location with a door enclosure has a smart mat (e.g., at the bottom of the drawer) that wirelessly exchanges information and provides power to the smart, lockable containers. In some embodiments, a transaction record is synchronized with the server at a later time if connectivity is not immediately available.

Some of the advantages of embodiments consistent with the present disclosure include a mobile dispensing system operating a cloud-based application wherein a user can authenticate access to resources available in the cloud (e.g., a medication inventory, a request for a medication, and the like) through a network. The mobile dispensing systems include devices having computing and networking capabilities such as found in an Internet-of-Things (IOT) configuration (e.g., "smart" devices), namely: Near Field Communication (NFC) protocols and devices, Bluetooth protocols and devices, and Bluetooth low-energy (BLE) protocols and devices and in addition Wi-Fi and cellular communications. More generally, a mobile dispensing system as disclosed herein may use radio-frequency (RF) circuitry, including antennas, transmitters, and receivers. Some devices also provide contactless or wireless power charging with an RF oscillating near field magnetic induction or with an RF oscillating, propagating electromagnetic field. Some devices are also configured for RF identification (RFID), low frequency (LF) identification, high frequency (HF) identification, and ultra-high frequency (UHF) identification, using propagating RF electromagnetic fields and associated circuitry.

Accordingly, in systems as disclosed herein, medications may be collected at a central pharmacy or at a point of collection from where medications are collected in containers having an RFID tag. Medication containers are transported to distributed locations at or near a medium size or smaller healthcare facility, where they are collected in a storage location with door enclosures (e.g., storage drawers) that also have RFID capabilities to identify the containers. All devices throughout the system are configured to identify the containers and determine their contents through RFID tagging and related capabilities. A healthcare professional may carry a mobile unit or cart having one or more storage locations with door enclosures and a mobile dispensing machine or computer that communicates with the storage location with door enclosures and the containers. The user may retrieve any desirable information for delivering medications from the containers in the storage location with door enclosures to a specific patient.

Current methods for medication management and delivery in distributed, smaller size healthcare facilities involve either paper based systems and non-secure storage at some or all points of distribution, or expensive high-capacity automated systems. Embodiments as disclosed herein improve upon existing methods by affording security, chain of custody, and full transactional controls in a system that scales from a single unit of measure (e.g., a secure container) to any number, without the need for monolithic conventional automated dispensing machines or physical hardware. Large machines typically constrain storage and delivery to a predetermined capacity that is not generally compatible with small capacity applications.

These systems and methods can provide the location and inventory at every point of origin and use for a healthcare system that is geographically dispersed and involves points of care that require a combination of high, medium, and low stock keeping unit (SKU) counts. Further, the number of SKU's at any point of use can generally be scaled up or down as demand requires without the installation or de-installation of hardware and other infrastructure. This is achieved through the logistics and distribution features of the system.

Some embodiments include a number of physical and software elements and workflows that comprise a scalable method for medication management and continuous inventory management.

FIG. 1 illustrates a system 100 for distributed medication management, according to some embodiments. A mobile dispensing machine 110 includes a memory 20, a processor 12, and a communications module 18. Memory 20 includes an application 22 and patient data 25. Patient data 25 may include information associated with patients that receive medications from mobile dispensing machine 110. Mobile dispensing machine 110 also includes an input device 14 (e.g., a mouse, a keyboard, a touch screen display, and the like) and an output device 16 (e.g., a display, a speaker, and the like). In some embodiments, input device 14 and output device 16 may include, at least partially, a smart mat configured to collect data from sensors and other devices associated with a patient that may be in close proximity to, or placed directly over the surface of, the smart mat. Accordingly, a user of mobile dispensing machine 110 may enter commands and queries to mobile dispensing machine 110 with input device 14, and receive graphic and other information from mobile dispensing machine 110 with output device 16.

Likewise, a centralized pharmacy server 130 includes a memory 40, a processor 36, and a communications module 38. In some embodiments, centralized pharmacy server 130 may include multiple servers 130 in a cloud-based architecture. Memory 40 may include patient data 45, which may be the same as patient data 25, or similar. Patient data 45 may include information associated with patients that receive medications from a centralized pharmacy. In some embodiments, patient data 45 includes patient data 25 and further information about other patients not associated with mobile dispensing machine 110. Memory 40 also includes medication data 47. In some embodiments, medication data 47 may further include an inventory list of all medications in the centralized pharmacy, and the patients associated with each. Further, in some embodiments, centralized pharmacy server 130 may be coupled with a medication database 160, which may be external to centralized pharmacy server 130.

Mobile dispensing machine 110 may be communicatively coupled with centralized pharmacy server 130 through a network 150, via communications module 18 in mobile dispensing machine 110 and communications module 38 in centralized pharmacy server 130. Network 150 can include, for example, any one or more of a local area network (LAN), a wide area network (WAN), the Internet, and the like. Further, network 150 can include, but is not limited to, any one or more of the following network topologies, including a bus network, a star network, a ring network, a mesh network, a star-bus network, tree or hierarchical network, and the like. Communications modules 18 and 38 may be configured to couple with network 150 to exchange information between mobile dispensing machine 110 and centralized pharmacy server 130. In some embodiments, communications modules 18 and 38 may be configured as a wireless communication hub, (e.g., under an IEEE 802.11.xx protocol, an IEEE 802.15.4 protocol, an NFC protocol, a Bluetooth protocol, a BLE protocol, and the like). Application 22 may include an IOT-based application having instructions to access centralized pharmacy server 130 and request, retrieve, provide, or update medical information from a patient.

Any one of processors 12 or 36 may include an embedded system micro controller and an operating system configured to execute instructions stored in any one of memories 20 and/or 40.

Figure 2:
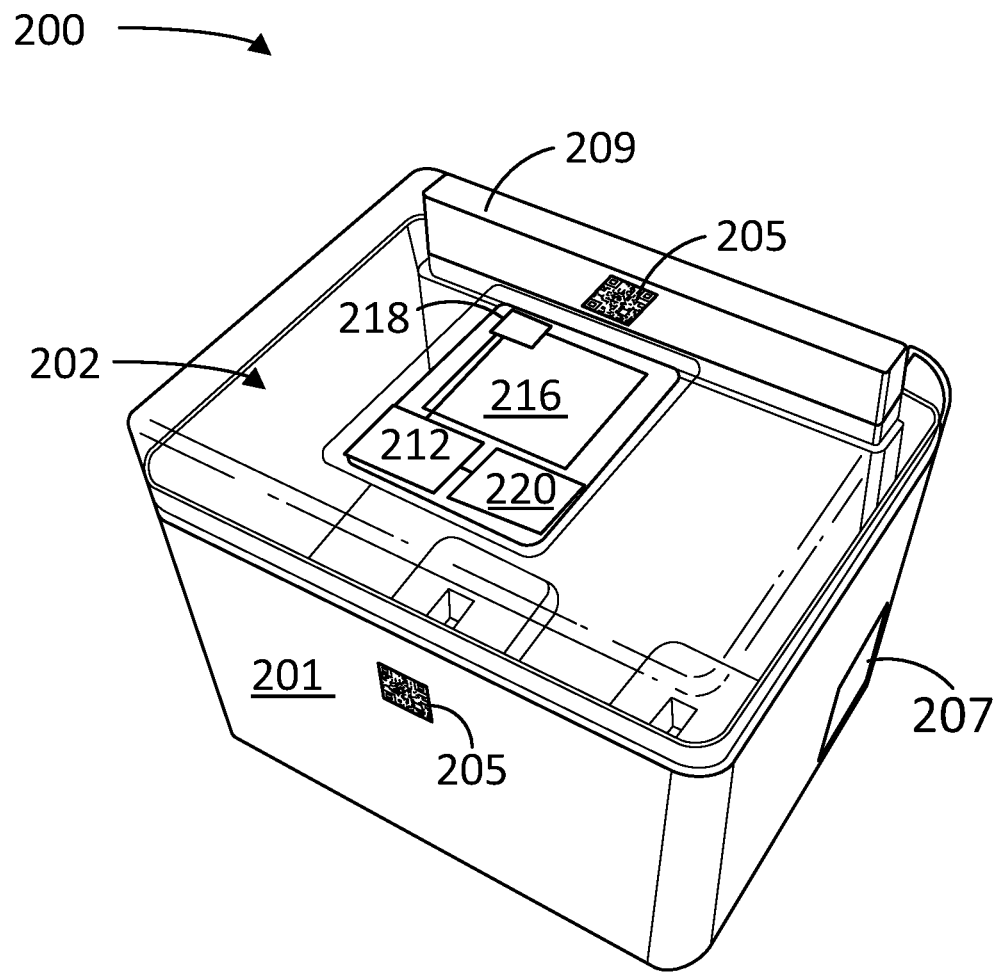
FIG. 2 illustrates a container for use in a medication dispensing unit, according to some embodiments.

FIG. 2 illustrates a container 200 for use in a medication dispensing unit, according to some embodiments. In some embodiments, container 200 may include an IOT cubie used for storage and dispensing medication.

Container 200 includes an electrically operable locking lid 202 on top of a body 201. A latch 209 secures lid 202 over body 201. In some embodiments, latch 209 is electrically operated and can be remotely accessed (e.g., by any one of mobile dispensing machine 110 or centralized pharmacy server 130, or a smartphone, tablet, mobile PC, web application and the like, operated and accessible by an authorized user). Container 200 is rugged and can be made in a variety of sizes and shapes. Container 200 may include a processor 212, a memory 220, a display 216, and a communications module 218. Container 200 also includes a tag 205, e.g., an RFID tag, a linear Barcode, or a two-dimensional 2D barcode (e.g., QR Code, and the like), with a unique identifier (preferably the same as a unique serial number). Accordingly, container 200 can be tracked and located by an external system (e.g., mobile dispensing machine 110 and or centralized pharmacy server 130) using for example BLE beacons, UHF RFID systems, Barcode scanners, QR Code scanners, and the like.

Processor 212 may be configured to execute instructions stored in memory 220 to perform, at least partially, steps in methods consistent with the present disclosure (e.g., processors 12 and 36, and memories 20 and 40). In some embodiments, display 216 may include an E-ink or other display technology that enables an electronic adjustment or update of the information on display 216. Display 216 may include a programmable label to display information (e.g., a unique serial number, a medication name, expiration date, a quantity of a medication stored in container 200, and the like). A power supply 207 (e.g., a battery, a transformer, a rechargeable battery, and the like) provides power to display 216, to processor 212, to memory 220, and to communications module 218. Power supply 207 may include circuits configured to transfer power from an external source. Communications module 218 may be configured for wireless communication and power, including, inter-alia, star and mesh GEN2 UHF RFID power and communications. A power supply 207 (e.g., a capacitor, a battery, or a Super Capacitor) provides power, wherein memory 220 may include instructions to cause processor 212 to perform a power management application to regulate the power usage from power supply 207.

Container 200 is constructed such that a successful, yet unauthorized, attempt to access its contents is tamper evident. In this manner, unauthorized use can be traceable to the last authorized user. In that regard, memory 220 may include a log file with a history of all access attempts (successful or not) to container 200.

Management of container 200 can be achieved remotely through standard forward and reverse logistic operations from mobile dispensing unit 110 and centralized pharmacy server 130. Containers 200 may be delivered to a point of care (e.g., patient's room, or bedside) on a scheduled or emergency basis. Further, medication empties, or below par units in container 200 may be returned to the centralized pharmacy for refill, or moved to another point of care, as desired.

FIGS. 3A-F illustrate multiple embodiments of a storage location with door enclosures 300A, 300B, 300C, 300D, 300E, and 300F (hereinafter, collectively referred to as "storage locations with door enclosures 300") to store multiple storage containers for use in a smart drawer or other storage location.

Figure 3A:
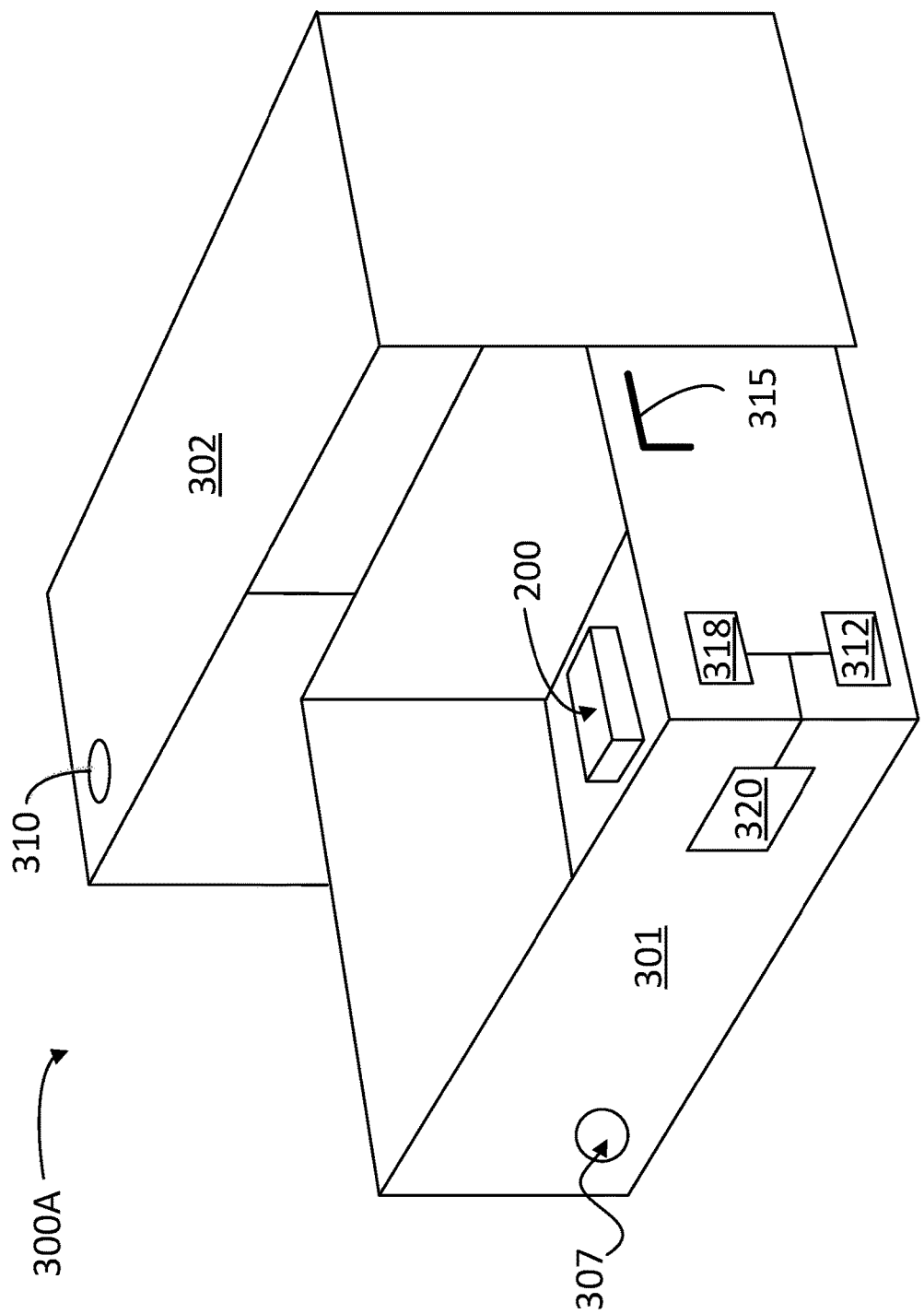
FIGS. 3A-F illustrate multiple embodiments of a storage location with a door enclosure to store multiple storage containers for use in a smart drawer or secure storage location.

FIG. 3A illustrates a storage location with one or more door enclosures 300A to store multiple storage containers 200 for use in a medication dispensing unit, according to some embodiments. More generally, storage location with door enclosures 300A may also store an assorted variety of RFID tagged items not enclosed in container 200, e.g., a pouch of medications and instruments such as needles, syringes, and the like. Storage location with door enclosures 300A includes an enclosure 301 covered by a lid 302, and a locking latch 315 to lock and unlock enclosure 301 with lid 302 based upon control signals received in an antenna 310 from an authorized user. A power inlet 307 may include an alternate current (AC) or a direct-current (DC) power inlet, or a power over Ethernet (POE) inlet, in which case power inlet 307 may also be configured to receive and provide Ethernet communications with a remote device through a network or cloud architecture (e.g., centralized pharmacy server 130 and network 150). Antenna 310 may include an RF circuitry to receive, process, and transmit RF signals. In some embodiments, antenna 310 includes an RFID tag identifier to receive information from one or more containers 200 stored inside enclosure 301. A communications module 318, in conjunction with antenna 310, interrogates the enclosed space of storage location with door enclosures 300A (e.g., scanning for RFID tags from container 200) and reports them to an external computer. A processor 312 is configured to control antenna 310 and to process information received in antenna 310, to execute instructions stored in a memory 320, to cause storage location with door enclosures 300A to perform, at least partially, steps in methods consistent with the present disclosure. Locking latch 315 may include an electronically actuated latch. Accordingly, communications module 318, in conjunction with antenna 310 and processor 312, may be configured to remotely actuate locking latch 315 to open or lock enclosure 301 with lid 302. In some embodiments, storage location with door enclosures 300A may use processor 312, communications module 318, and memory 320 to operate as an automated medication dispensing machine. In some embodiments, enclosure 301 may also include different types of devices next to container 200, such as sensors (e.g., temperature sensors), beacons, authentication devices, and the like.

Figure 3B:
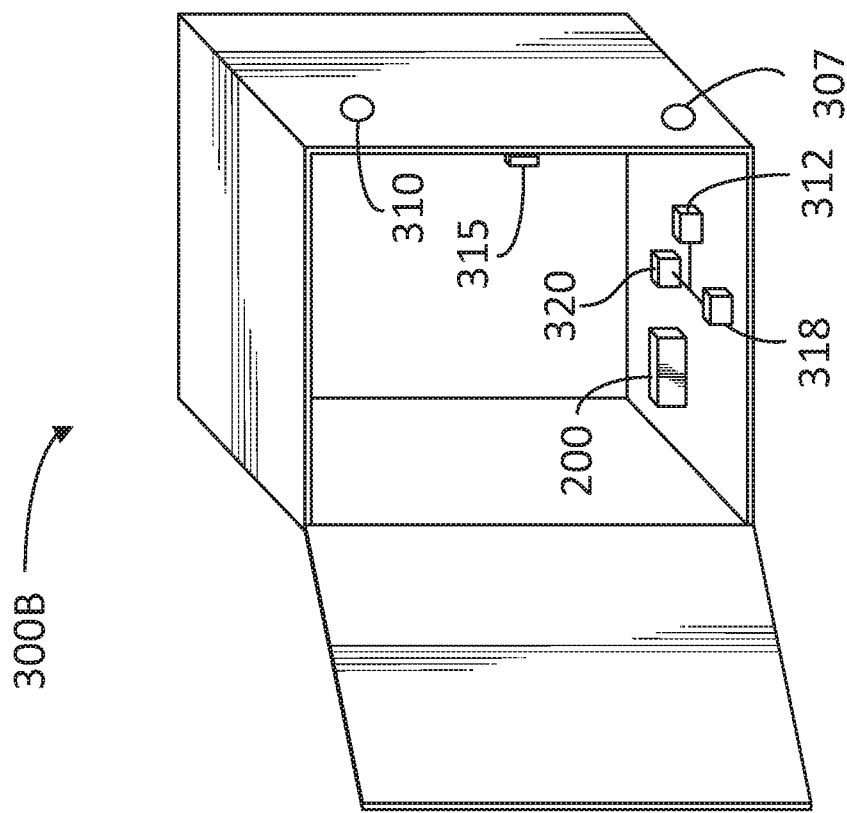

FIG. 3B illustrates a storage location with one or more door enclosures 300B to store multiple storage containers for use in a smart drawer/storage location. Storage location with door enclosures 300B includes two versions: one with a single door enclosure opening to one side of the storage, and one with two doors that open on either side of the storage, closing at the middle of the front side. Storage location with door enclosures 300B includes antenna 310, locking latch 315, and power inlet 307, as described in detail above.

Figure 3C:
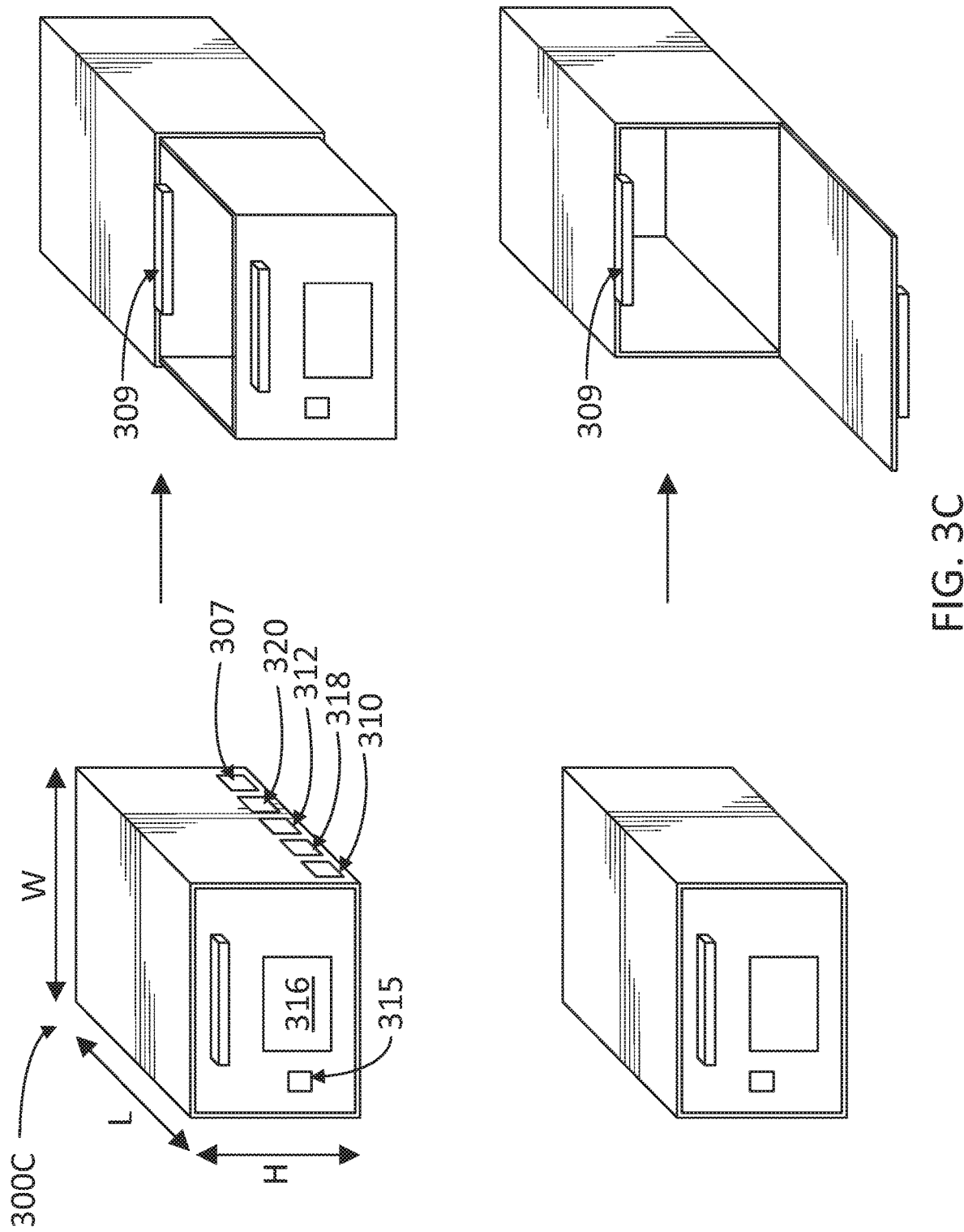

FIG. 3C illustrates a storage location with one or more door enclosures 300C to store multiple storage containers for use in a smart drawer/storage location. Storage location with door enclosures 300C includes a power inlet 307, a memory 320, a processor 312, a communications module 318, and a wireless antenna 310. Locking latch 315 opens a drawer containing the medications. Storage location with door enclosures 300C also includes a panel 316 (e.g., update display 216). In some embodiments, panel 316 may include an E-ink or other display technology that enables an electronic adjustment or update of the information on panel 316. Panel 316 may include a programmable label to display information (e.g., a unique serial number, a medication name, an expiration date, a quantity of a medication stored in storage location with door enclosure 300C, and the like). A latch 309 secures the lid for supervised opening (e.g., latch 209).

Figure 3D:
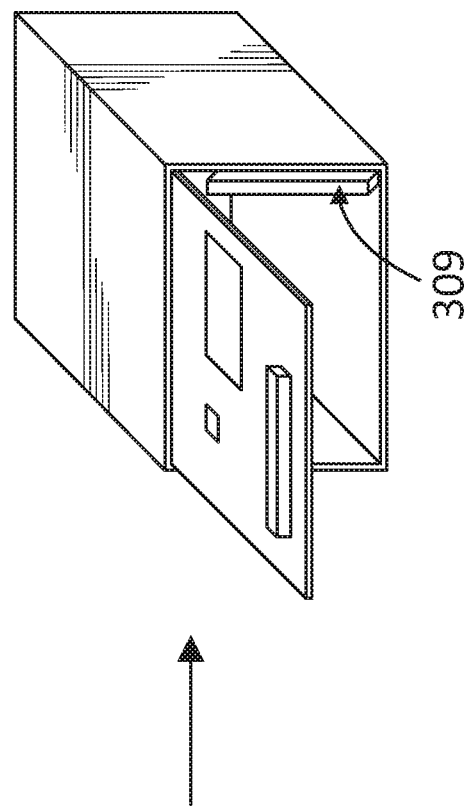
Figure 3D:
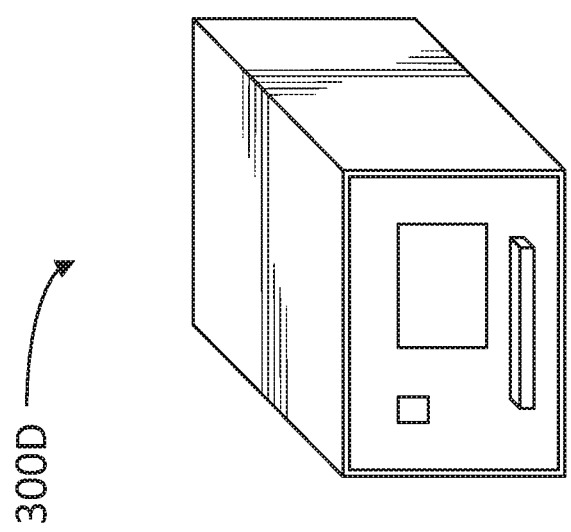

FIG. 3D illustrates a storage location with one or more door enclosures 300D to store multiple storage containers for use in a smart drawer/storage location. Latch 309 is as described above in relation to storage location with enclosure 300C.

Figure 3E:
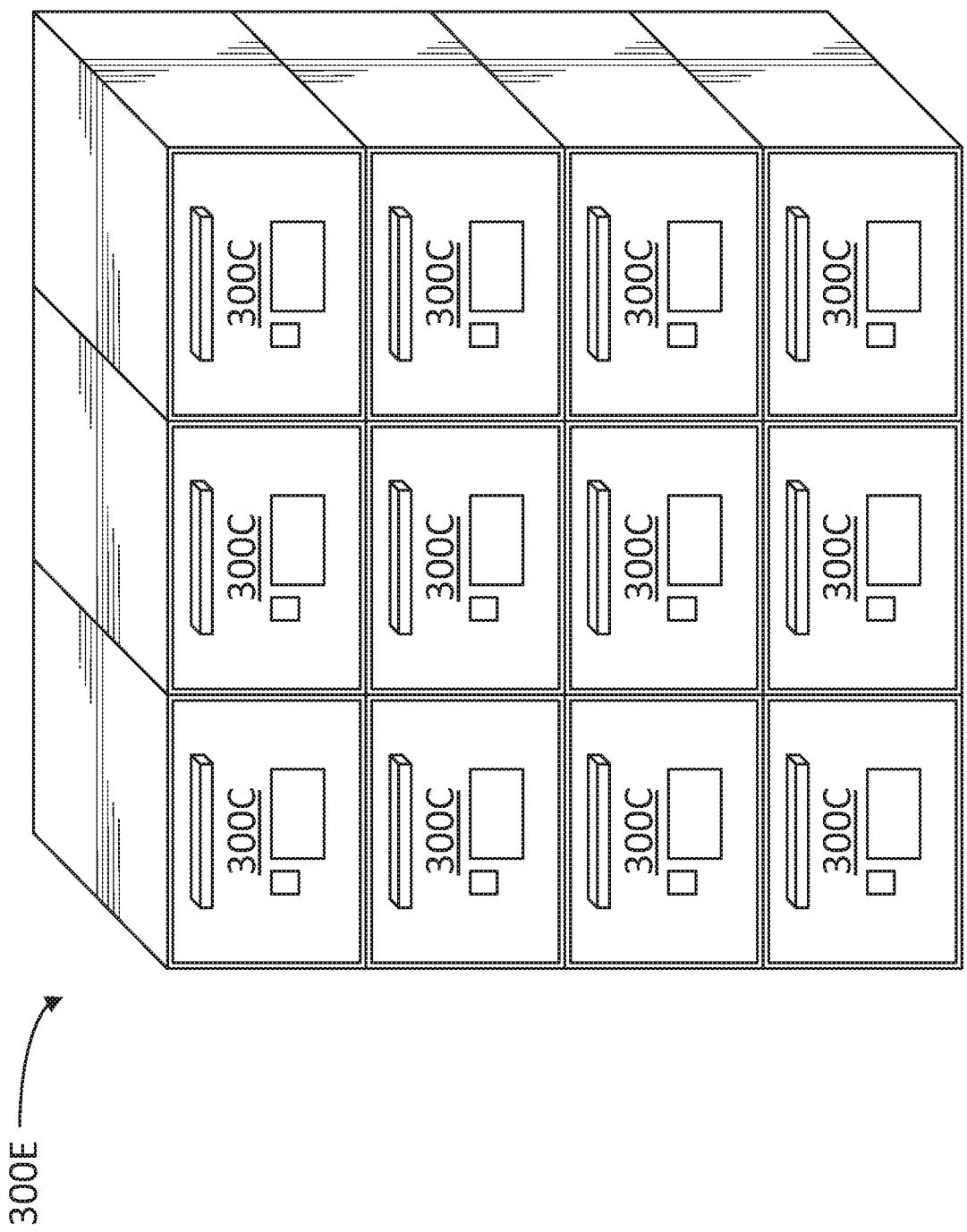

FIG. 3E illustrates a storage location with one or more door enclosures 300E to store multiple storage containers for use in a smart drawer/storage location. In some embodiments, storage location with door enclosures 300E is a modular stack of multiple storage locations with door enclosures 300C.

Figure 3F:
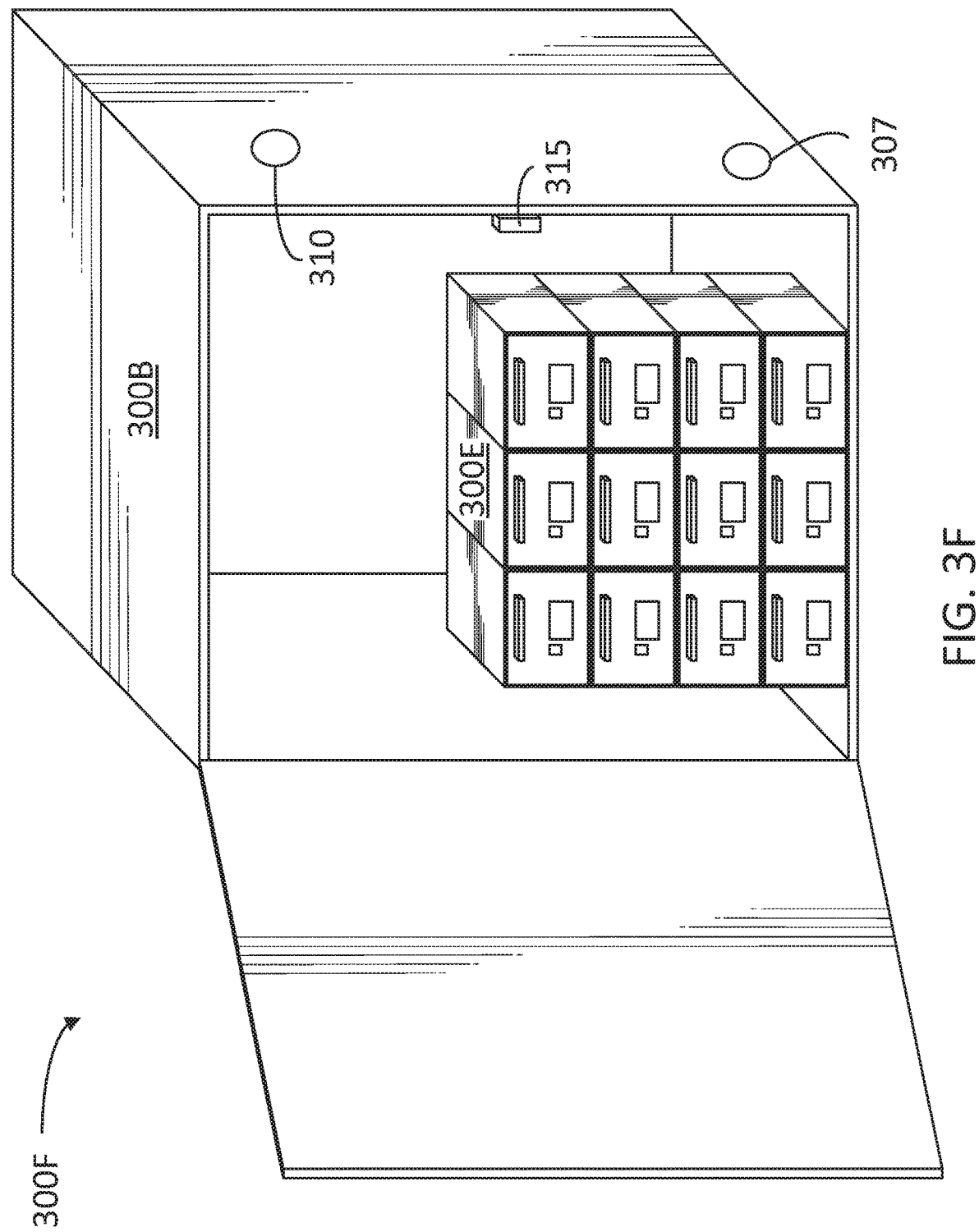

FIG. 3F illustrates a storage location with one or more door enclosures 300F to store multiple storage containers for use in a smart drawer/storage location. Accordingly, storage location with door enclosures 300F includes storage location with door enclosure 300E inside a storage location with door enclosure 300B.

Figure 4:
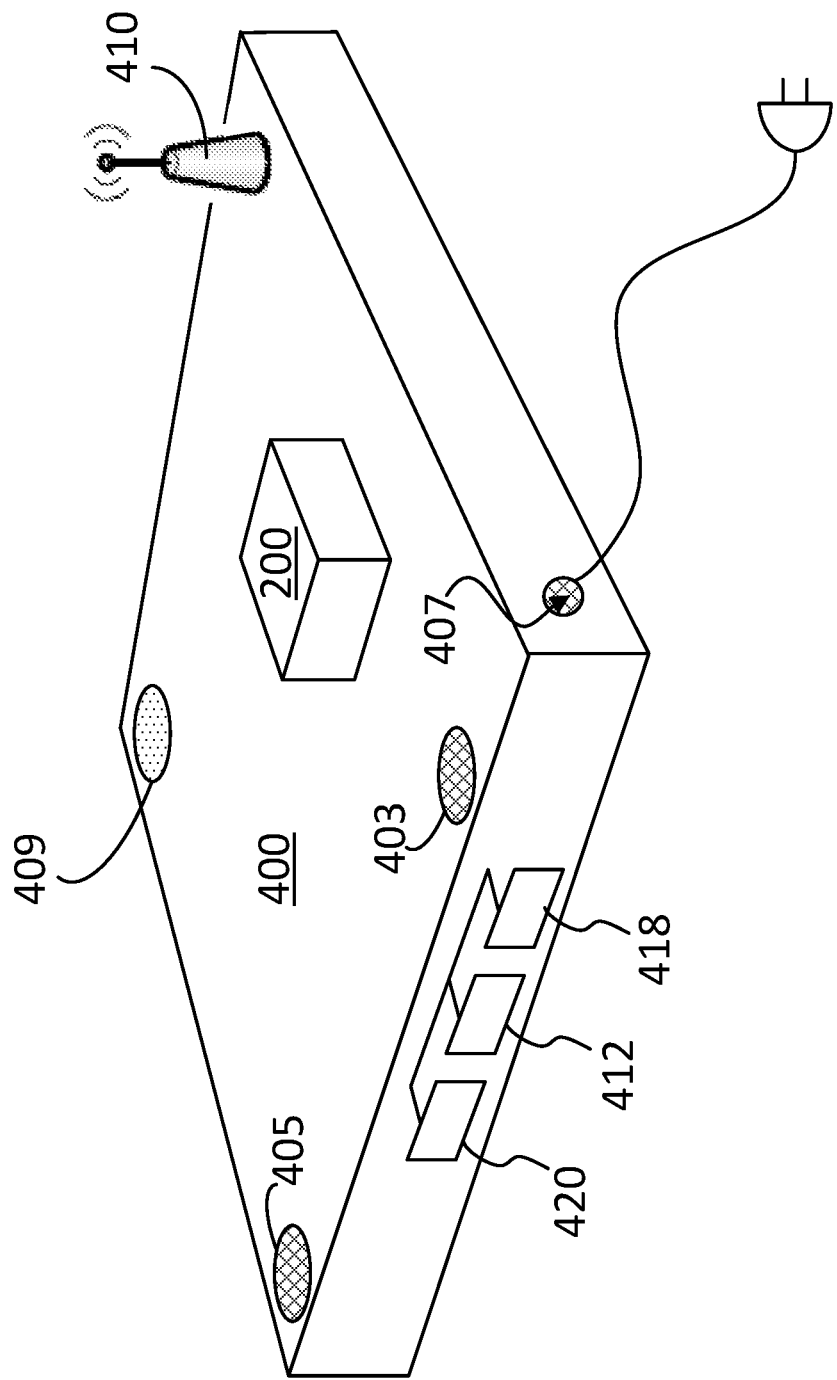
FIG. 4 illustrates a mat for use in a medication dispensing unit, according to some embodiments.

FIG. 4 illustrates an electronically operated control unit or "mat 400" that provides power and communications, wired or wirelessly, to a container 200. Mat 400 may be used in a medication dispensing unit, according to some embodiments. While mat 400 is depicted in a planar, square shape, in some embodiments it may include different form factors and more complex surface shapes (e.g., adapted to be laid over three-dimensional objects). In some embodiments, mat 400 may be a network appliance communicably coupled to any one of mobile dispensing machine 110, centralized pharmacy server 130, or any mobile device handled by an authorized user (e.g., medical personnel) through a communications module 418 (e.g., communications modules 18 and 38). Communications module 418 may enable mat 400 to communicate with a server or multiple servers in a cloud architecture (e.g., centralized pharmacy server 130), or local computers in the vicinity of mat 400. Accordingly, in some embodiments, mat 400 may be integrated with a local application level computing device. Electronic components in container 200 may be configured to become fully functional when placed over mat 400. A processor 412 may communicate with processor 212 in container 200 to transfer data, status and commands, and operate lid 202 (e.g., open and/or lock lid 202 and processors 12 and 36), and change, adjust, or update display 216. In some embodiments, processor 412 may be configured to execute commands stored in a memory 420 (e.g., memories 20 and 40) to perform at least partially steps in methods consistent with the present disclosure. An identity management port 403 enables a user access to wirelessly open the smart container.

In some embodiments, processor 412 may include an IOT gateway. Accordingly, mat 400 may operate as an IOT gateway for sensors and other devices and appliances communicably coupled with mat 400. In that regard, the sensors and devices communicating with mat 400 may include "self-powered" devices that may not be required to be in close proximity to mat 400 (e.g., temperature sensors, authentication devices, beacons, and other peripherals within a patient's room). In some embodiments, processor 412 enables mat 400 to do local processing (e.g., perform control operations on, or inventory operations from data provided by, devices and appliances), as well as communicate to a server or cloud application (e.g., centralized pharmacy server 130).

In some embodiments, mat 400 is configured to provide power and communicate with "energy harvesting" devices (e.g., container 200). To this effect, mat 400 may include a contactless charging device 405 to wirelessly provide power to power supply 207 in container 200. Accordingly, contactless charging device 405 may be configured to provide inductive or resonant power through a near field, RF oscillating magnetic field, a propagating, resonant RF electromagnetic field, or an optical charging device (e.g., through a light emitting diode or laser). The choice of charging strategy in contactless charging device 405 may vary according to a desirable application or device to be charged, and the range and power available from contactless charging device 405, and the power desired to charge the external device.

Mat 400 may be configured to receive devices having a variable form factor or "any surface" smart devices, on or near its surface. Devices placed on mat 400 may be configured to receive power from contactless charging device 405 and communicate with a computer or other cloud based devices (e.g., smartphones, tablets, mobile computers, and the like) to operate the device (e.g., container 200). Other devices that may be placed on and interact with mat 400 may include display modules, sensor modules, identification modules, third party devices, consumer devices, and the like. Additionally, mat 400 may receive and interact with other self-powered mobile devices having additional range, such as BLE beacons, sensors, and even smart phones. In that regard, a device or appliance communicatively coupled to, and interacting with, mat 400, may not be placed directly on top of the surface of mat 400, and may be within range of any of multiple communications protocols between mat 400 and the device or appliance. Communications module 418 may also be configured to communicate with a network (e.g., network 150), a local computer, and other devices, as desired in some applications.

Mat 400 may include a power inlet 407. In some embodiments, power inlet 407 may include an alternate current (AC) or a direct-current (DC) power inlet, or a power over Ethernet (POE) inlet, in which case power inlet 407 may also be configured to receive and provide Ethernet communications with a remote device through a network or cloud architecture (e.g., centralized pharmacy server 130 and network 150). In some embodiments, mat 400 includes a sensor 409 configured to determine a physical property of the device placed on the mat surface (e.g., weight, size, and shape). Accordingly, sensor 409 may include an electric sensor, a magnetic sensor, an optical sensor (e.g., a photodetector or a video camera), or a mechanical sensor. Mat 400 may also include an antenna 410. In some embodiments, antenna 410 is an identification device, which may include an RFID antenna (e.g., a GEN2 RFID reader/antenna) to provide RFID power in addition to reading identification data from container 200. In some embodiments, antenna 410 may include an NFC identification reader, or an LF or HF identification reader. Antenna 410 may be configured to perform multiple forms of communication, or may include more than one type of antenna (e.g., Wi-Fi, Bluetooth, and the like). In some embodiments, the communication between mat 400 and any appliance or device placed on its surface, or in sufficient proximity to mat 400 may include, in addition to, an identification signal, sensor data, inventory data, maintenance data, and control information to operate a device (e.g., open or close a lid, a drawer, update a display, and the like).

In some embodiments, mat 400 may include sensors (e.g., a weight sensor) to determine a physical property of a device deposited on its surface (e.g., the weight and/or size of container 200). Further, processor 412 may be configured to process the physical property of the device as relevant information that may be stored in memory 420, or transmitted to the centralized pharmacy server through communications module 418. For example, in some embodiments, mat 400 may be configured to track devices, materials, and equipment that are placed (inadvertently or not) by healthcare personnel directly on mat 400 or within range of communications module 418.

When processor 412, memory 420, and communications module 418 incorporate a Gen 2 UHF RFID option, then mat 400 may be configured to open and access any secure enclosure for RFID tagged items that is placed on mat 400 (e.g., storage location with door enclosures 300A). For example, in some embodiments, mat 400 may power and operate a latch for a lid of the secure enclosure (e.g., latch 315 and lid 302).

In some embodiments, mat 400 may be integrated with a local, application-level, computing device. Further, in some embodiments, mat 400 can be instantiated or configured as a HUB or Gateway device that allows smart devices to communicate and optionally be powered on mat 400. For example, in some embodiments, mat 400 may be configured to receive data from inside a patient's room, or in proximity to a patient's bed. Accordingly, the mat may receive patient identification data (e.g., from a beacon placed next to the patient's bed), and other medical data associated with the patient, including a bodily temperature (e.g., from a temperature sensor inside the patient), a room temperature, or a cardio-respiratory condition (e.g., heart rate, air volume in respiration, and the like). In yet other embodiments, mat 400 may be configured to provide and update medication information about a patient that is in close proximity to mat 400 as soon as a nurse or other medical personnel places a portable computer (e.g., a smartphone, tablet, or any other mobile computer device) over the surface of mat 400.

In some embodiments, mat 400 may be configured to form a bottom surface in storage location with door enclosures 300A (e.g., the floor of storage location with door enclosures 300A, cf. FIG. 3A). More generally, any side of storage location with door enclosures 300A, including lid 302, may be configured at least partially as mat 400. Accordingly, mat 400 may communicate with storage location with door enclosures 300A via antennas 410 and 310 in mat 400 and storage location with door enclosures 300A, respectively. Further, mat 400 may communicate directly with container 200 and any other device inside enclosure 301, and perform inventory operations or alert communications based on the received data. For example, a sensor inside enclosure 301 may be a temperature sensor indicating that the contents of container 200 may desirably be replaced, disposed, removed, or storage location with door enclosures 300A may need to be moved to a different location.

Figure 5:
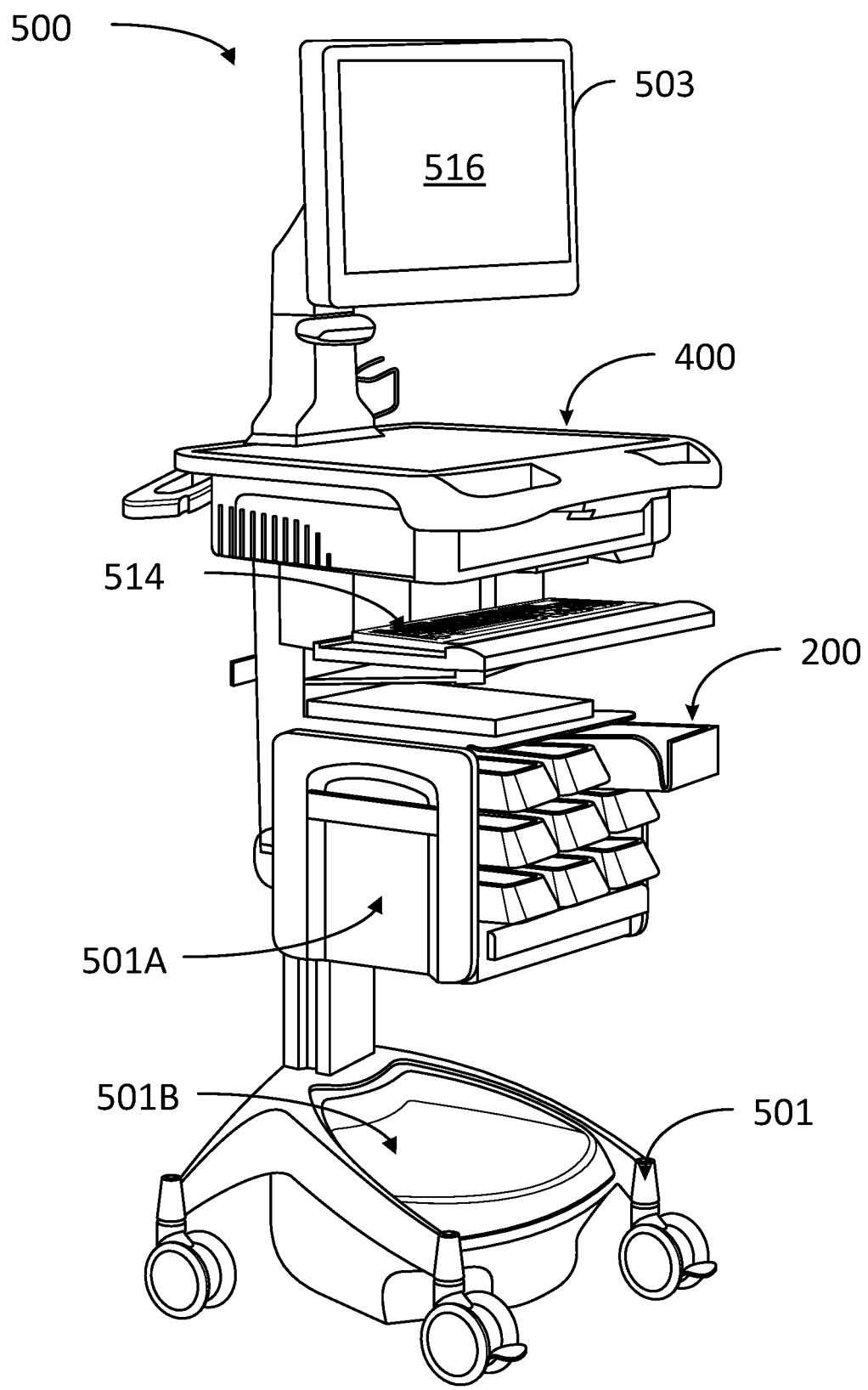
FIG. 5 illustrates a mobile medication dispensing unit, according to some embodiments.

FIG. 5 illustrates a mobile medication dispensing unit 500, according to some embodiments. Mobile medication dispensing unit 500 may include a cart 501 having wheels to allow a healthcare professional to carry mobile medication dispensing unit 500 from the proximity of a first patient to the proximity of a second patient. Mobile medication dispensing unit 500 may include a plurality of containers 200 stored within a storage location with door enclosures 501A (e.g., any one of storage location with door enclosures 300). Additionally, in some embodiments, medication dispensing unit 500 includes mat 400 in communication with a computer 503 including a display 516. An input device 514 (e.g., a keyboard, mouse, pointer, and the like) may be coupled to computer 503, so that a user may provide commands and request actions from computer 503. Accordingly, certain aspects of mobile medication dispensing unit 500 may be as described above, regarding mobile dispensing machine 110. More specifically, mobile medication dispensing unit 500 may include the features and capabilities of the above described mobile dispensing machine 110 (cf. FIG. 1). Mobile medication dispensing unit 500 may be transported to a location in proximity to a point of medication dispensing (e.g., patient's bedside, operating room, and the like). In some embodiments, multiple storage location with door enclosures 501B can be arranged in a vertical stack of different plan view dimensions to achieve specific storage capacities (hereinafter, collectively referred to as "storage locations with door enclosures 501"). Thus, mobile medication dispensing unit 500 can conveniently scale from one or two storage locations with door enclosures 501A and 501B to any number (e.g., three, four, or even more). Moreover, mobile medication dispensing unit 500 may include location tracking capabilities (e.g., beacons, real-time location systems (RTLS), radio-frequency identification (RFID) tags, and the like).

Medications stored in container 200 may be refilled, replaced, or emptied by healthcare personnel through mobile medication dispensing unit 500, using computer 503 to communicate with centralized pharmacy server 130. Accordingly, a user (e.g., healthcare personnel) may receive instructions from centralized pharmacy server 130 to refill, replace, or empty the contents of one or more containers 200. The user then may carry the one or more containers 200, or storage location with door enclosures 501 to a centralized pharmacy, where the contents of the one or more container 200 are refilled, replaced, or emptied. The user may also return, introduce to, or remove from storage location with door enclosures 501 one or more containers 200 per instructions from centralized pharmacy server 130. In some embodiments, the user may have authorization to access storage location with door enclosures 501 and any one of containers 200 to increment or decrement a quantity of contained items at the user's discretion. In such configurations, a registry of the items retrieved and their quantity may be logged in the memory of computer 503, and transmitted to centralized pharmacy server 130 to update patient data 45 and medication data 47. In some embodiments, container 200 performs an RFID coupling directly with a processor in mobile medication dispensing unit 500 (e.g., processor 412).

Further information such as the association of the user (e.g., identity, level of authorization, link to a patient, and the like), the serial number of container 200, or the quantity and description of items inside container 200 including metadata (e.g., expiration date) may be retrieved remotely by mobile medication dispensing unit 500 from centralized pharmacy server 130.

Mobile medication dispensing unit 500 ensures the physical security of medications delivered to patients, regardless of the distance to the centralized pharmacy, e.g., during transport. Thus, items stored in containers 200 are conveniently and securely distributed to and back from geographically distant points of use. At the point of use, containers 200 are received and can be stored in storage location with door enclosures 501.

Figure 6:
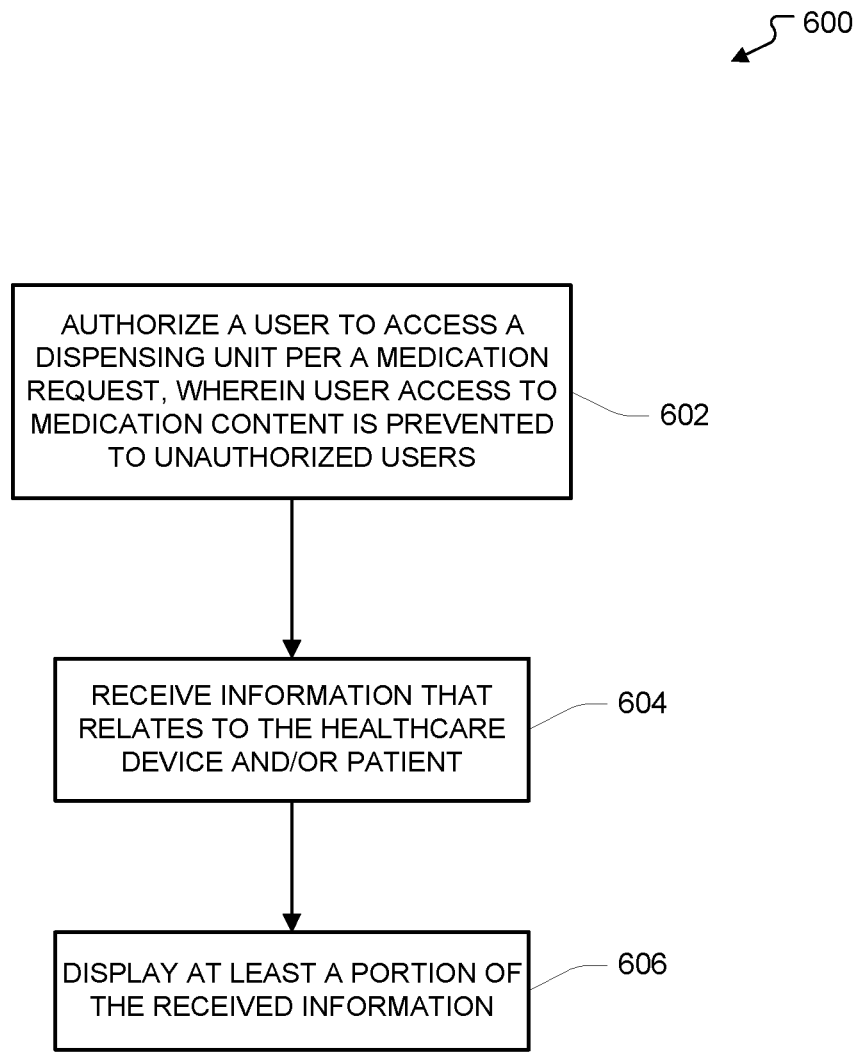
FIG. 6 illustrates a flowchart with steps in a method for distributed medication dispensing, according to some embodiments.

FIG. 6 illustrates a flowchart with steps in a method 600 for distributed medication dispensing, according to some embodiments. At least some of the steps in method 600 may be performed by a computer having a processor executing commands stored in a memory of the computer (e.g., mobile dispensing machine 110, centralized pharmacy server 130, mat 400, processors 12, 36, 212, 312, or 412, and memories 20, 40, 220, or 420). At least some of the steps in method 600 may be performed by a mobile medication dispensing device, including one or more storage locations with door enclosures, each storage location with door enclosures having at least one or more containers, the containers including medications or any other tagged items (e.g., medication dispensing device 500, containers 200, storage location with door enclosures 300A, and mat 400). In some embodiments, steps in method 600 may be partially performed by a mobile dispensing machine and by a centralized pharmacy server being communicatively coupled with one another via communications modules, through a network (e.g., communications modules 18 and 38, and network 150). Further, steps as disclosed in method 600 may include retrieving, editing, and/or storing files in a database that is part of, or is communicably coupled to, the computer (e.g., medication database 160). Methods consistent with the present disclosure may include at least some, but not all, of the steps illustrated in method 600, performed in a different sequence. Furthermore, methods consistent with the present disclosure may include at least two or more steps as in method 600, performed overlapping in time, or almost simultaneously.

Step 602 includes authorizing a user access to the dispensing unit per a medication request. In some embodiments, step 602 includes authorizing a user to access a storage location with door enclosures in the mobile dispensing machine by the centralized pharmacy server. User access to medication content is prevented to unauthorized users.

Step 604 includes indicating to the user a storage location with door enclosures in the dispensing unit associated with the medication request.

Step 606 includes displaying a list for the user with one or more medications in the storage location with door enclosures that are indicated in the medication request.

Step 608 includes providing to the user access to the storage location with door enclosures. In some embodiments, step 608 may include remotely actuating a latch to open a lid in the storage location with door enclosures.

Step 610 includes providing a visual indicator to the user for a selected container in the storage location with door enclosures associated with the medication request. In some embodiments, step 610 may include blinking a light-emitting diode (LED) in the selected container (e.g., in red, green, or blue color). In some embodiments, step 610 may include adjusting a display in the selected container so that it attracts the visual attention of the user (e.g., a blinking sign on the display, and the like). In some embodiments, step 610 may further include providing an audio indicator (e.g., a beep, a buzz, and the like) to the container, or a mechanical indicator (e.g., a vibration mode, and the like).

Step 612 includes providing to the user access to the at least one storage container. In some embodiments, step 612 may include unlocking the selected container for the user (e.g., by wirelessly actuating a latch for a lid in the at least one storage container from the mat). Accordingly, in some embodiments, step 612 may include receiving the storage container on a surface of a mat that is configured to recognize the selected container and unlock a lid in the selected container upon recognition. In some embodiments, step 612 includes transmitting an NFC, Bluetooth, or BLE command and the like to a processor in the selected container (e.g., mat 400), to unlock the container lid, or to release a latch in the container lid.

Step 614 includes determining a medication content in the selected container based on a medication retrieval or a medication addition by the user.

Step 616 includes displaying for the user a verification list (e.g., in the visual indicator) with at least some of the medications retrieved or added to the at least one storage container.

Step 618 includes locking the at least one storage container when the user has verified the transaction. In some embodiments, step 618 may include receiving the selected container on the mat surface configured to wirelessly actuate the latch for the lid in the selected container.

Step 620 includes updating a record and a medication inventory in the remote server based on the transaction. When the user verifies the transaction information displayed in the visual indicator, the medication content of the selected container is determined. In some embodiments, step 620 may include scanning of the contents of the storage location with door enclosures and of each of the containers stored therein, and reporting the serial numbers of tags in the storage location with door enclosures. In some embodiments, step 620 may include updating the contents of the storage location with door enclosures, including serial numbers for new and removed containers since the storage location with door enclosures was last unlocked. In this manner, the location of containers 200 and any other tagged items that may be stored in the storage location with door enclosures can be determined. In some embodiments, step 620 may include accessing the centralized pharmacy server to update databases in the mobile dispensing machine and in the centralized pharmacy server. An alert may be displayed to the user when a medication content of a selected container is not verified by the server.

Figure 7:
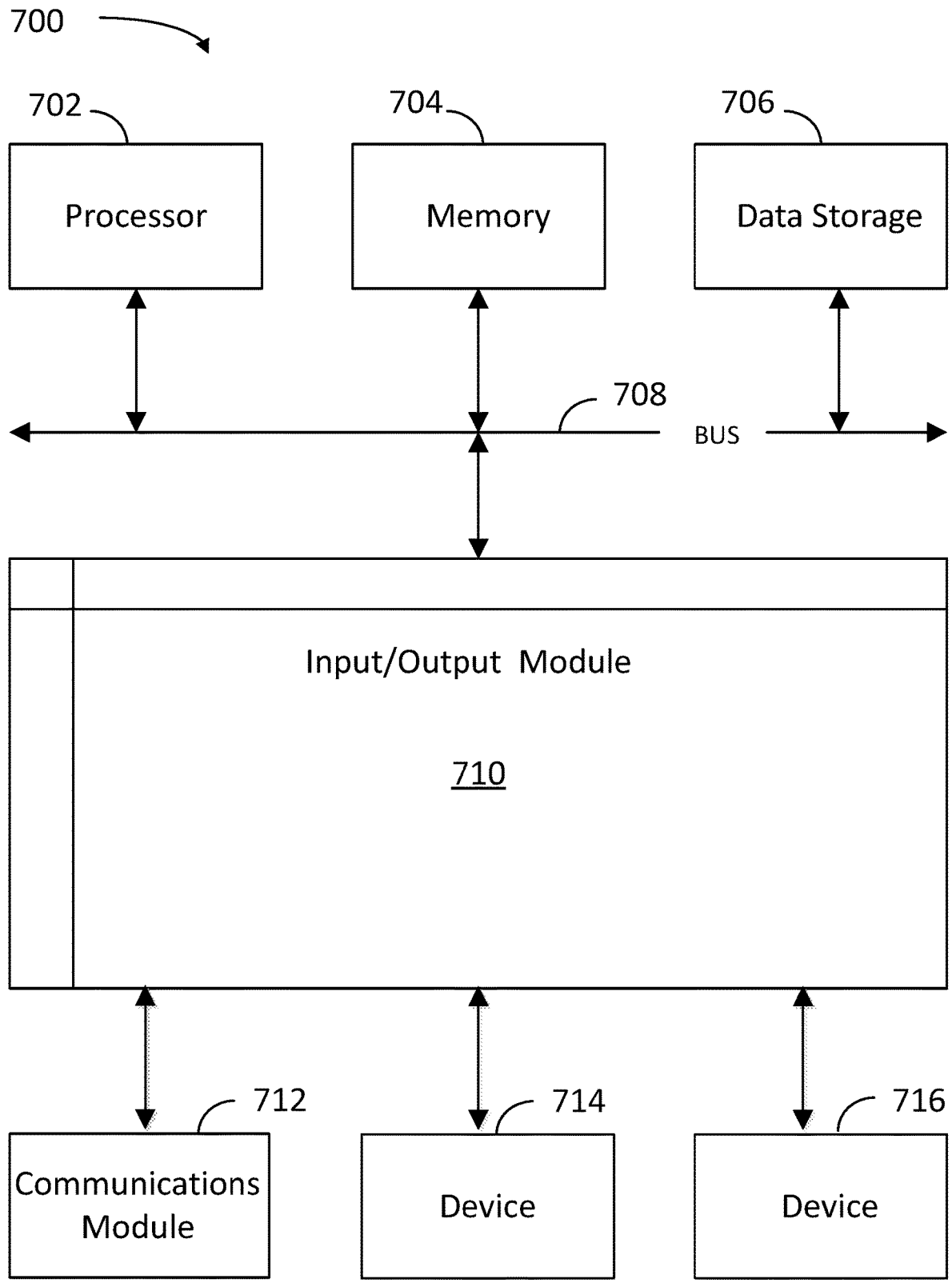
FIG. 7 is a block diagram illustrating an example computer system for distributed medication dispensing, according to some embodiments.

FIG. 7 is a block diagram illustrating an example computer system 700 with which the methods and steps illustrated in method 600 can be implemented, according to some embodiments. In certain aspects, computer system 700 can be implemented using hardware or a combination of software and hardware, either in a dedicated server, integrated into another entity, or distributed across multiple entities.

Computer system 700 includes a bus 708 or other communication mechanism for communicating information, and a processor 702 coupled with bus 708 for processing information. By way of example, computer system 700 can be implemented with one or more processors 702. Processor 702 can be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. In some embodiments, processor 702 may include modules and circuits configured as a "placing" tool or engine, or a "routing" tool or engine, to place devices and route channels in a circuit layout, respectively and as disclosed herein.

Computer system 700 includes, in addition to hardware, code that creates an execution environment for the computer program in question, e.g., code that constitutes processor firmware, a protocol stack, a database management system, an operating system, or a combination of one or more of them stored in an included memory 704, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 708 for storing information and instructions to be executed by processor 702. Processor 702 and memory 704 can be supplemented by, or incorporated in, special purpose logic circuitry.

The instructions may be stored in memory 704 and implemented in one or more computer program products, i.e., one or more modules of computer program instructions encoded on a computer readable medium for execution by, or to control the operation of, the computer system 700, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, Wirth languages, embeddable languages, and xml-based languages. Memory 704 may also be used for storing temporary variable or other intermediate information during execution of instructions to be executed by processor 702.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 700 further includes a data storage device 706 such as a magnetic disk or optical disk, coupled to bus 708 for storing information and instructions.

Computer system 700 is coupled via input/output module 710 to various devices. The input/output module 710 is any input/output module. Example input/output modules 710 include data ports such as USB ports. The input/output module 710 is configured to connect to a communications module 712. Example communications modules 712 include networking interface cards, such as Ethernet cards and modems. In certain aspects, the input/output module 710 is configured to connect to a plurality of devices, such as an input device 714 and/or an output device 716. Example input devices 714 include a keyboard and a pointing device, e.g., a mouse or a trackball, by which a user can provide input to the computer system 700. Other kinds of input devices 714 are used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 716 include display devices, such as an LED (light emitting diode), CRT (cathode ray tube), or LCD (liquid crystal display) screen, for displaying information to the user.

Methods as disclosed herein may be performed by computer system 700 in response to processor 702 executing one or more sequences of one or more instructions contained in memory 704. Such instructions may be read into memory 704 from another machine-readable medium, such as data storage device 706. Execution of the sequences of instructions contained in main memory 704 causes processor 702 to perform the process steps described herein (e.g., as in method 600). One or more processors in a multi-processing arrangement may also be employed to execute the sequences of instructions contained in memory 704. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 700 includes servers and personal computer devices. A personal computing device and server are generally remote from each other and typically interact through a communication network. The relationship of client and server arises by virtue of computer programs running on the respective computers and having a client-server relationship to each other. Computer system 700 can be, for example, and without limitation, a desktop computer, laptop computer, or tablet computer. Computer system 700 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 702 for execution. Such a medium may take many forms, including, but not limited to, non-volatile media, volatile media, and transmission media. Non-volatile media include, for example, optical disks, magnetic disks, or flash memory, such as data storage device 706. Volatile media include dynamic memory, such as memory 704. Transmission media include coaxial cables, copper wire, and fiber optics, including the wires that comprise bus 708. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

In one aspect, a method may be an operation, an instruction, or a function and vice versa. In one aspect, a clause or a claim may be amended to include some or all of the words (e.g., instructions, operations, functions, or components) recited in other one or more clauses, one or more words, one or more sentences, one or more phrases, one or more paragraphs, and/or one or more claims.

To illustrate the interchangeability of hardware and software, items such as the various illustrative blocks, modules, components, methods, operations, instructions, and algorithms have been described generally in terms of their functionality. Whether such functionality is implemented as hardware, software, or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise," as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public, regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A method, comprising:
   authorizing a user to access a dispensing unit upon receipt of a medication request indicating one or more requested medications, wherein the dispensing unit comprises one or more door enclosures within the dispensing unit, each door enclosure configured open and close to store at least one container having a display;
   identifying a selected container stored in the one or more door enclosures, the selected container comprising the one or more requested medications;
   receiving the selected container on a surface of a planar electronic mat forming a bottom surface of a respective door enclosure of the one or more door enclosures and configured to recognize the selected container based on a first transmission between a radio-frequency identification (RFID) tag of the selected container and an RFID antenna of the electronic mat when the selected container is placed over the surface of the electronic mat in the respective door enclosure, and to wirelessly unlock a lid of the selected container upon recognizing the selected container with the electronic mat;
   receiving, by the electronic mat, the first transmission responsive to receiving the selected container over the surface of the electronic mat;
   unlocking the lid of the selected container by wirelessly actuating a latch of the lid of the selected container responsive to a second wireless transmission of a command from the electronic mat to the selected container that is generated responsive to the recognition of the selected container with the electronic mat;
   receiving, by the electronic mat, medical data associated with a patient in proximity to the electronic mat;
   updating, by the electronic mat, medication information about the patient responsive to placing a portable computer over the surface of the electronic mat;
   verifying a transaction comprising the medication request; and
   updating a record and a medication inventory in a remote server based on the transaction.

2. The method of claim 1, wherein identifying the selected container comprises providing a visual indicator in a display of the selected container.

3. The method of claim 2, wherein the respective door enclosure comprises a plurality of containers, and wherein the visual indicator further visually indicating to the user the selected container as being associated with the medication request, from among the plurality of containers.

4. The method of claim 2, further comprising updating the visual indicator in the display of the selected container according to the record and the medication inventory in the remote server.

5. The method of claim 2, further comprising determining a medication content of the selected container when the user has verified transaction information displayed in the visual indicator.

6. The method of claim 1, further comprising wirelessly providing power to the selected container from the electronic mat, wherein the selected container includes electronic components, including the latch of the lid, that are configured to become functional when placed over the electronic mat, wherein the electronic mat powers and operates the latch.

7. The method of claim 1, wherein wirelessly actuating the latch of the lid comprises wirelessly providing, from the RFID antenna of the electronic mat, the second wireless transmission to unlock the lid of the selected container.

8. The method of claim 1, further comprising:
   providing for display by the selected container an alert when a medication content of the selected container is not verified by the remote server; and
   preventing access to the medication content to a user who is not authorized to use the selected container.

9. The method of claim 1, further comprising displaying a list for the user, the list comprising at least one medication of the one or more requested medications that is in the one or more door enclosures.

10. The method of claim 1, further comprising:
    receiving, by the electronic mat, from a sensor within the selected container when the selected container is placed over the surface of the electronic mat, sensor data including whether the contents of the selected container should be replaced, disposed, or removed, or the one or more door enclosures should be moved to a new location.

11. A dispensing device, comprising:
    one or more door enclosures within the dispensing device, each door enclosure configured to store at least one container having an identification tag, wherein each said door enclosure can be in an open or a closed position, wherein the dispensing device is configured to:
   authorize a user to access a dispensing unit based on receipt of a medication request indicating one or more requested medications;
   identify a selected container stored in a respective door enclosure of the one or more door enclosures, the selected container comprising one or more requested medications;
   verify a transaction comprising the medication request; and
   update a record and a medication inventory in a remote server based on the transaction;
an electronically actuated latch;
an electronic mat configured to form a bottom surface of the respective door enclosure, comprising:
   an antenna configured to scan for the identification tag in the respective door enclosure when the respective door enclosure is the closed position;
   a processor, configured to control the antenna and to process information received in the antenna;
   a communications module to update a database in a remote server based on a content of the at least one container and processed by the processor,
   wherein the electronic mat is configured to:
      recognize the selected container based on a first transmission between a respective identification tag of the selected container and the antenna of the electronic mat when the selected container is placed over the surface of the electronic mat in the respective door enclosure;
      wirelessly unlock the lid of the selected container by wirelessly actuating a latch of the lid of the selected container responsive to a second wireless transmission of a command from the electronic mat to the selected container that is generated responsive to the recognition of the selected container with the electronic mat;
      receive medical data associated with a patient in proximity to the electronic mat; and
      update the received medical data associated with the patient responsive to placing a portable computer over the surface of the electronic mat.

12. The dispensing device of claim 11, wherein the antenna is a radio-frequency antenna and the identification tag is an active radio-frequency identification tag emitting a beacon signal.

13. The dispensing device of claim 11, wherein the respective door enclosure and the lid are configured to confine an electromagnetic radiation inside the device when the lid is closed.

14. The dispensing device of claim 11, wherein the antenna is configured to receive a content information from the selected container, and the processor is further configured to verify the content information with the database in the remote server.

* * * * *